US008783194B2

(12) United States Patent
Sleat et al.

(10) Patent No.: US 8,783,194 B2
(45) Date of Patent: Jul. 22, 2014

(54) MARKING APPARATUS FOR NUCLEIC ACID MARKING OF ITEMS

(75) Inventors: Robert Sleat, Cardiff (GB); Greg Van Lint, Zaventem (BE)

(73) Assignees: Trace Tag International Limited, London (GB); 3SI Security Systems, Inc., New York, NY (US)

( * ) Notice: Subject to any disclaimer, the term of this patent is extended or adjusted under 35 U.S.C. 154(b) by 1418 days.

(21) Appl. No.: 10/508,416

(22) PCT Filed: Mar. 21, 2003

(86) PCT No.: PCT/GB03/01199
§ 371 (c)(1),
(2), (4) Date: Feb. 7, 2005

(87) PCT Pub. No.: WO03/080931
PCT Pub. Date: Oct. 2, 2003

(65) Prior Publication Data
US 2006/0121181 A1    Jun. 8, 2006

(30) Foreign Application Priority Data

Mar. 22, 2002    (GB) .................... 0206820.3

(51) Int. Cl.
| | | |
|---|---|---|
| E05G 1/00 | (2006.01) | |
| E05G 5/00 | (2006.01) | |
| C12Q 1/68 | (2006.01) | |
| C12P 19/34 | (2006.01) | |
| C12M 1/00 | (2006.01) | |
| C07H 21/02 | (2006.01) | |
| C07H 21/04 | (2006.01) | |
| E05G 1/14 | (2006.01) | |

(52) U.S. Cl.
CPC ... E05G 1/14 (2013.01); C12Q 1/68 (2013.01)
USPC .................. 109/25; 109/20; 109/23; 435/6.1; 435/91.1; 435/91.2; 435/283.1; 536/23.1; 536/24.33

(58) Field of Classification Search
CPC .............. E05G 1/14; E05G 5/00; C12Q 1/68; C12Q 1/686; C12Q 1/6806
USPC .............. 109/20, 23, 25; 435/6.1, 91.1, 91.2, 435/283.1; 536/23.1, 24.33
See application file for complete search history.

(56) References Cited

U.S. PATENT DOCUMENTS

| | | | |
|---|---|---|---|
| 5,139,812 A | | 8/1992 | Lebacq |
| 5,512,439 A | | 4/1996 | Hornes et al. |
| 5,598,793 A | | 2/1997 | Lopez, Jr. |
| 5,643,728 A | * | 7/1997 | Slater et al. .................. 435/6.16 |
| 5,666,435 A | * | 9/1997 | Burgi et al. .................... 382/129 |
| 5,904,848 A | * | 5/1999 | Wong et al. .............. 210/500.36 |
| 6,060,237 A | * | 5/2000 | Nygren et al. ................ 435/6.19 |
| 6,103,474 A | * | 8/2000 | Dellinger et al. ............. 435/6.14 |
| 6,261,809 B1 | * | 7/2001 | Bertling et al. ............... 435/91.2 |
| 6,712,011 B2 | * | 3/2004 | Fumanelli ........................ 109/20 |

FOREIGN PATENT DOCUMENTS

| | | |
|---|---|---|
| AU | 200187321 A1 | 11/2000 |
| DE | 44 39 896 A1 | 11/1994 |
| EP | 0623658 A2 | 11/1994 |
| EP | 0623902 A2 | 11/1994 |
| EP | 0 744 012 | 1/1995 |
| EP | 1488039 B1 | 6/2006 |
| FR | 2 775 693 | 3/1998 |
| GB | 849396 | 9/1960 |
| GB | WO0106464 * | 1/2001 |
| WO | WO 89/10977 | 11/1989 |
| WO | WO 91/17265 | 11/1991 |
| WO | WO 91/17265 A1 | 11/1991 |
| WO | WO 95/02702 | 1/1995 |
| WO | WO 96/17954 | 6/1996 |
| WO | WO 98/03758 | 1/1998 |
| WO | WO 98/13523 | 4/1998 |
| WO | WO 98/28440 | 7/1998 |
| WO | WO 00/40750 | 7/2000 |
| WO | WO 00/43540 | 7/2000 |
| WO | WO 00/44891 | 8/2000 |
| WO | WO 00/61799 | 10/2000 |
| WO | WO 01/36676 A3 | 5/2001 |
| WO | WO 02/18636 | 3/2002 |
| WO | WO 02/18636 A2 | 3/2002 |
| WO | WO 02/40355 A3 | 5/2002 |
| WO | WO 02/085341 A2 | 10/2002 |
| WO | WO 03/038000 A1 | 5/2003 |
| WO | WO 03/080931 A1 | 10/2003 |

OTHER PUBLICATIONS

Minerals technical brochure.*
Meares et al, A novel seeding technique for the flow visualization of pressurized air flows, 1997, Meas. Sci. Technol., 8, 1183-1186.*
Sleat, Commodity tracing and DNA, 2000, Sensor Review, 20, 282-286.*
Minerals technical brochure, downloaded from the internet [www.galleries.com], pp. 1-2, downloaded from the internet on Nov. 23, 2008.*
Mears et al, A novel seeding technique for the flow visualization of pressurized air flows, 1997, Meas. Sci. Technol. 8, 1183-1186.*
Communication in European Patent Application No. 03712388.Feb. 2402, mailed Feb. 2, 2005.
Response to Communication (Feb. 2, 2005) in European Patent Application No. 03712388.2-2402, mailed Jun. 27, 2005.

(Continued)

*Primary Examiner* — Narayan Bhat
(74) *Attorney, Agent, or Firm* — Clark & Elbing LLP (57) ABSTRACT

A marking apparatus (1) for marking an item (12). The apparatus comprises: means to receive the item; a nucleic acid marker; means to release a marking fluid (8); and a distribution mechanism (11) coupled to the nucleic acid marker and the means to release the marking fluid. The means to release the marking fluid can be activated to release the marking fluid such that the distribution mechanism disperses a mixture of the nucleic acid marker and the marking fluid onto the item.

41 Claims, 2 Drawing Sheets

(56) References Cited

OTHER PUBLICATIONS

Opposition in European Patent Application No. 03712388.2-2402, mailed Mar. 7, 2007, in the French language.
Response to Opposition (Mar. 7, 2007) in European Patent Application No. 03712388.2-2402, mailed Dec. 20, 2007.
International Search Report for PCT/GB2003/01199, mailed Aug. 13, 2003.
International Preliminary Report on Patentability for PCT/GB2003/01199, completed Jun. 7, 2006.
Document A10 cited in Opposition Proceedings for EP1488039, letter from AXYTRANS to Jurispatent dated May 3, 2007. English translation provided.
Document A11 cited in Opposition Proceedings for EP1488039, letter from AXYTRANS to Jurispatent dated Jun. 1, 2001. English translation provided.
Document A12 cited in Opposition Proceedings for EP1488039, letter from SRPJ to AXYTRANS dated Jun. 17, 2001. English translation provided.
Document A13 cited in Opposition Proceedings for EP1488039 dated Apr. 28, 2000. English translation of Article 8 provided.
Document A14 cited in Opposition Proceedings for EP1488039, Order of Apr. 28, 2000 Laying Down the Technical Conditions Necessary for the Consent Required by Article 8 of Decree No. 2000-376 of Apr. 28, 2000 Relating to Transport of Funds. English translation provided.
Document A15 cited in Opposition Proceedings for EP1488039, letter from Mrs. Denis (Scientific Police Laboratory of Lyons) to Mr. Brient (AXYTRANS) dated May 3, 2007. English translation provided.
English translation of Notice of Opposition (EP1488039).
File History of U.S. Appl. No. 09/958,840 from Oct. 15, 2001 through Feb. 6, 2009.
U.S. Appl. No. 09/958,840, filed Jan. 28, 2002, Minton et al.

\* cited by examiner

MARKING APPARATUS FOR NUCLEIC ACID MARKING OF ITEMS

CROSS REFERENCE TO RELATED APPLICATIONS

This application is the U.S. National Stage of International Application No. PCT/GB03/01199, filed Mar. 21, 2003, which, in turn, claims the benefit of GB 0206820.3, filed Mar. 22, 2002.

The present invention relates to a marking apparatus and also to a method of marking an item and a method of analysing a marked item.

In the field of security, it is often necessary to transport large quantities of bank notes securely between locations. For example, it is common to transport bank notes from a bank vault to an automated teller machine (ATM) situated in a supermarket or shopping centre where they can be dispensed. Although the bank notes are guarded whilst in transit, they are inherently vulnerable to theft in view of the need to transport them in civilian vehicles, especially during the time between the unloading of the vehicle and the deposit of the bank notes in the ATM. This attracts thieves due to the large amount of money that is involved.

Typically, when money is transported to an ATM, it is locked inside a cassette before its departure and the entire cassette is loaded into the ATM, together with the bank notes. This avoids the need for direct handling of the bank notes, which can be a security risk. Thus any thief attempting to steal the bank notes must be able to penetrate the cassette in order to remove the bank notes and use them.

It is known in the art to defend the bank note cassettes in a number of ways. It is, of course, possible to provide a physical locking mechanism on the cassette, which helps to prevent it from being broken open. However, the problem with this approach is that a thief can steal the entire cassette, with the bank notes inside, and then open the cassette in a secret location where he has appropriate cutting tools in order to retrieve the bank notes. Thus, given sufficient time, a thief will be able to open most cassettes, despite a physical locking mechanism being in place.

It is also known in the art to supplement the physical locking mechanism of a cassette with a device which renders the bank notes unusable upon tampering with the cassette. Typically, such a device comprises a reservoir of ink and a source of pressurised gas. When tampering with the cassette is detected, the pressurised gas is released and used to disperse the ink across the bank notes held in the cassette (see, for example, WO-A-98/03758). In such arrangements, if a thief is able to steal a cassette containing bank notes, he will, on attempting to open the cassette, trigger the release of the ink which indelibly colours each of the bank notes in a clearly visible manner. The ink cannot be removed from the bank note by washing etc. without also destroying the bank note itself. This makes the subsequent use of the bank notes impossible because shops and banks will refuse to accept bank notes which have been stained in this way. Accordingly, while these devices do not prevent the theft of bank notes per se, they render such theft unprofitable because the bank notes cannot be used.

Despite the widespread use of such bank note staining devices in the cassettes used to transfer bank notes, there is still a significant problem with the theft of bank note cassettes. On average, there are several such thefts each day in the UK, alone. It is commonly the case that the police will recover large quantities of stained bank notes following such thefts, the bank notes having been dumped by thieves who realise that they will be unable to use them. However, the bank notes are not necessarily valueless to their original owner since, if he can be identified, central banks will usually reimburse the value of bank notes that have been indelibly stained and recovered. The problem is that there are so many thefts of bank notes that it is often difficult to determine exactly which consignment of bank notes has been recovered at any particular time and thus who the rightful owner of the bank notes is. Thus it is difficult to ascertain who the rightful owner of the bank notes is. Without this information, reimbursement cannot take place.

This is particularly a problem in the countries of the so-called "Euro-zone" in which bank notes are equally usable in any of the member countries. Therefore the large number of bank notes in circulation makes it even more difficult to determine in which particular theft any recovered bank notes were stolen.

The problems associated with the transport of bank notes have been exemplified above in relation to the supply of money to ATMs. However, the problems also arise in the transfer of bank notes in other situations such as between bank vaults and when bank notes are carried by an individual in a brief case or the like.

The present invention seeks to alleviate one or more of the above problems.

According to a first aspect of the present invention, there is provided a marking apparatus for marking an item, the apparatus comprising: a nucleic acid marker; means to release a marking fluid; and a distribution mechanism coupled to the nucleic acid marker and the means to release the marking fluid, the means to release the marking fluid being activatable to release the marking fluid such that the distribution mechanism disperses a mixture of the nucleic acid marker and the marking fluid onto the item.

Preferably, the apparatus further comprises means to receive the item.

Conveniently the item is one or more bank notes, the means to release the marking fluid being activatable to release the marking fluid such that the mixture of the nucleic acid marker and the marking fluid is dispersed onto the one or more bank notes.

Advantageously, the apparatus is an automated teller machine cassette.

Preferably the means to release the marking fluid comprises a reservoir of marking fluid.

Alternatively the marking fluid comprises an indelible ink.

Conveniently the nucleic acid marker is mixed in with the reservoir of ink.

Advantageously the marking apparatus further comprises a nucleic acid reservoir containing the nucleic acid marker, the nucleic acid reservoir being coupled to the distribution mechanism such that when the marking fluid reservoir is activated, the distribution mechanism mixes the marking fluid and the nucleic acid marker.

Alternatively the means to release a marking fluid comprises one or more smoke pellets, the marking fluid comprising smoke.

Preferably the means to release the marking fluid and the distribution mechanism comprise a pyrotechnic device containing the one or more smoke pellets.

Preferably the nucleic acid marker comprises a plurality of single-stranded DNA oligonucleotides.

Advantageously each DNA oligonucleotide comprises a variable region flanked by first and second generic regions on either side, there being minimal homology between the variable region and the generic regions.

Conveniently each DNA oligonucleotide comprises a variable region flanked by first and second generic regions, the variable region containing no consecutively repeated nucleotides.

Preferably the marking apparatus further comprises a detector connected to the means to release the marking fluid, the detector activating the means to release the marking fluid in response to detecting tampering with the marking apparatus.

Advantageously the marking apparatus further comprises a plurality of carrier particles to which the nucleic acid marker is attached.

Conveniently the carrier particles are made from a polymer.

Preferably the carrier particles are made from an inorganic compound, more preferably magnesium silicate hydroxide.

Advantageously the nucleic acid marker is attached to the carrier particles via a covalent bond.

Conveniently each nucleic acid marker molecule is bonded to a linker molecule, the linker molecule having a covalent bond to a carrier particle.

Preferably the linker molecule is a $C_{12}$-$C_{16}$ alkyl group.

Alternatively the nucleic acid marker is attached to the carrier particles via ionic interactions or passive adsorption.

Preferably the marking apparatus further comprises a fluorescent label attached to the carrier particles.

According to a second aspect of the present invention, there is provided a bank note storage system comprising a plurality of marking apparatuses as described above, wherein the nucleic acid markers each have a respective variable region flanked by first and second generic regions, the first and second generic regions being the same on all of the nucleic acid markers and the variable regions being different in the nucleic acid markers of each marking apparatus.

According to a third aspect of the present invention, there is provided a method of security marking an item comprising the steps of: providing a mixture of a nucleic acid marker and a marker fluid; and dispersing the mixture onto the item.

Conveniently the method further comprises the step of identifying the nucleic acid marker.

Preferably the method further comprises the step of, prior to providing a mixture of the nucleic acid marker and the marker fluid, selecting the nucleic acid marker from a pool of nucleic acid markers, each marker in the pool having a respective variable region flanked by first and second generic regions, the first and second generic regions being the same on all of the nucleic acid markers in the pool and the variable regions being different on each marker in the pool.

According to a fourth aspect of the present invention, there is provided a method of analysing an item that has been marked with a marker fluid and a nucleic acid marker, comprising the steps of: identifying the nucleic acid marker.

Conveniently, the step of identifying the nucleic acid marker comprises sequencing at least a portion of the nucleic acid marker.

Preferably, the step of identifying the nucleic marker comprises: providing a plurality of test oligonucleotides; applying the nucleic acid marker to the test oligonucleotides under conditions such that the nucleic acid marker hybridizes to test oligonucleotides to which it is complementary; and determining the test oligonucleotide or oligonucleotides to which the nucleic acid marker has hydrodised.

Advantageously, the test oligonucleotides are attached to a substrate in an array formation.

Preferably the item is a bank note, but is alternatively one or more credit cards, cellular phone recharging cards, tickets such as lottery tickets or confidential storable documents.

Advantageously the method further comprises the step of amplifying the number of copies of the nucleic acid marker sequence prior to the step of sequencing at least a portion of the nucleic acid marker.

Conveniently the amplifying step comprises using thermal cycling nucleic acid amplification, preferably PCR, to amplify the number of copies of the nucleic acid marker sequence.

Alternatively, the amplifying step comprises using an isothermal amplification technique.

Preferably the method further comprises the step of measuring the quantity of amplified nucleic acid in the polymerase chain reaction during the amplifying step and stopping the amplification after the quantity of amplified nucleic acid reaches a predetermined threshold.

Advantageously the step of measuring the quantity of amplified nucleic acid comprises the step of adding an intercalating dye to the amplified nucleic acid.

Conveniently the nucleic acid marker comprises a plurality of single-stranded DNA oligonucleotides.

Preferably each DNA oligonucleotide comprises a variable region flanked by first and second generic regions on each side, there being minimal homology between the variable region and the generic regions.

Advantageously each DNA oligonucleotide comprises a variable region flanked by first and second generic regions, the variable region containing no consecutively repeated nucleotides.

Conveniently the method comprises using the marking apparatus described above.

Preferably, the method further comprises the step of removing the nucleic acid marker from the carrier particles.

Advantageously the method further comprises the step of visualising the fluorescent label and determining the location of the fluorescent label on the item.

According to a fifth aspect of the present invention, there is provided a marking apparatus for marking an item, the apparatus comprising: a pyrotechnic device containing one or more smoke pellets; a dye; and a nucleic acid marker, the dye and nucleic acid marker being impregnated into the smoke pellets, the pyrotechnic device being activatable to release a mixture of smoke, the dye and the nucleic acid marker.

According to a sixth aspect of the present invention, there is provided a method of producing a marking apparatus comprising: providing a pyrotechnic device containing one or more smoke pellets having a dye incorporated therein; preparing a mixture of a nucleic acid marker and a solvent; and positioning the mixture on to at least one of the smoke pellets such that the mixture diffuses through the smoke pellets.

Preferably the mixture comprises between 60 and 90% alcohol and between 10 and 40% water.

In certain aspects of the present invention, the step of measuring the quantity of amplified nucleic acid is used in methods of analysing an item that has been marked with a nucleic acid marker but that has not been marked with a marker fluid.

It is to be understood that, in certain aspects of the present invention, the marking apparatus is not provided with means to receive the item. In these aspects of the invention, the marking apparatus is a separate module that can be attached to a suitable means to receive the item.

In this specification a "marking fluid" means a fluid that visibly stains an item.

In this specification a "fluid" means any liquid or gas, including smoke, that has the properties of a fluid.

In this specification, the phrase "identifying a nucleic acid marker" means determining sufficient information about the marker such that it can be differentiated from any other nucleic acid marker. In some embodiments this comprises sequencing the nucleic acid marker. However in other embodiments sequencing, as such, does not take place because the nucleic acid marker is identified by, for example, determining that it is identical to another nucleic acid marker.

In this specification, the word "comprising" means "including" or "consisting of" and the word "comprises" means "includes" or "consists of".

In order that the present invention may be more readily understood, and so that further features thereof may be appreciated, embodiments of the invention will now be described, by way of example, with reference to the accompanying drawings in which.

BRIEF DESCRIPTION OF THE DRAWINGS

Figure 1:
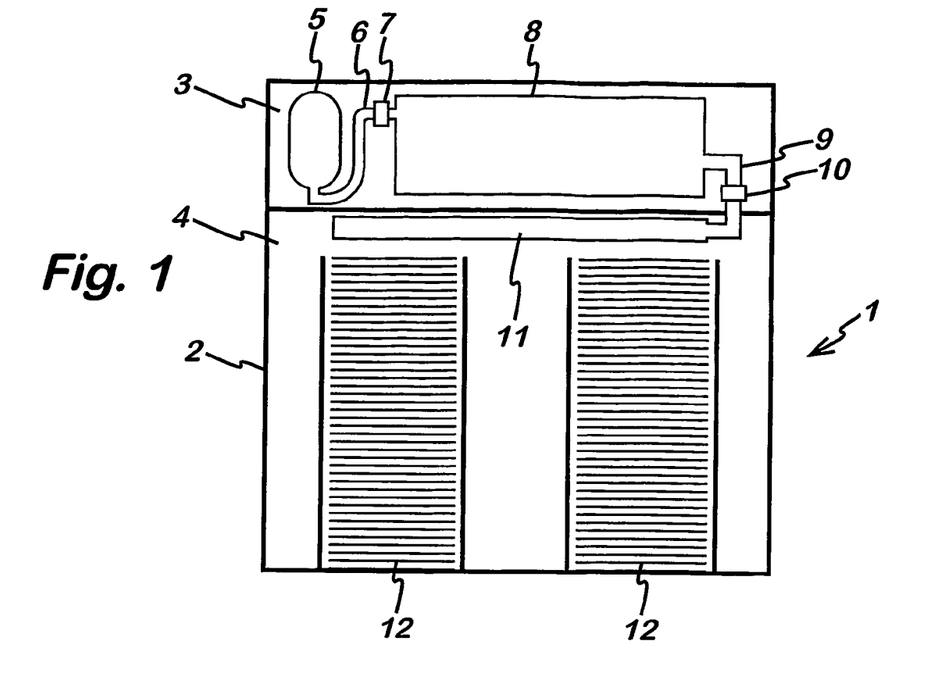
FIG. 1 is a cross-sectional view of a bank note cassette in accordance with one embodiment of the present invention.

Referring to FIG. 1, a bank note cassette 1 comprises an outer housing 2, divided into a marking compartment 3 and a bank note storage compartment 4. The bank note cassette 1 is of a type for insertion into an ATM.

The marking compartment 3 contains a canister 5 of pressurised gas connected via a pipe 6 and an actuator 7 to an ink reservoir 8. The ink reservoir 8 contains 200 ml of indelible ink mixed with 1 ml of DNA in buffer, such that there is a total of between 5 and 80 nmoles of DNA in the indelible ink.

The ink is such that it is difficult to resolublize or lead away. In some embodiments the ink is an alcohol soluble dye with a pigment and a surface active agent in an organic solvent such as industrialised methylated spirits. An exemplary ink is disclosed in EP-A-0623658.

The DNA is added to the ink while the ink is in the ink reservoir 8, the ink and DNA being mixed up and the reservoir 8 subsequently sealed. The DNA is of a particular sequence which will be described in greater detail below.

A outlet pipe 9 leads from the ink reservoir 8, via a pressure valve 10 to a distribution arm 11. The outlet pipe 9 passes into the bank note storage compartment 4 of the housing 2 such that the distribution arm 11 is located in the bank note storage compartment. The distribution arm 11 is provided with numerous perforations (not shown) which allow the exit and dispersion of ink from the distribution arm 11. Located adjacent the distribution arm 11, within the bank note storage compartment 4, are two stacks of bank notes 12 received in channels. A mechanism (not shown) is provided to allow release of the bank notes 12 once the cassette 1 has been inserted into an ATM.

In use, the contents of the marking compartment 3 and the distribution arm 11 are inactive while the cassette 1 is transported and the bank notes 12 are removed from an ATM under normal circumstances. However, if the cassette 1 is tampered with, a detection mechanism (not shown) sends a signal to the actuator 7 to release the contents of the canister 5 such that the pressurised gas forces itself into the ink reservoir 8. This raises the pressure within the ink reservoir 8 and the portion of the outlet pipe 9 leading up to the pressure valve 10. When the pressure in the ink in the pipe 9 reaches a predetermined level, the pressure valve 10 releases itself and the ink and DNA mixture are forced out of the reservoir 8, through the remainder of the outlet pipe 9 and into the distribution arm 11 where they are sprayed over the stacks of bank notes 12. Thus the distribution arm 11 disperses the ink and DNA mixture. The arm is located so that all of the bank notes 12 are covered with the mixture of ink and DNA. Furthermore, the ink and DNA mixture is dispersed with such force that a portion of it leaves the bank note storage compartment 4 and sprays around the exterior of the cassette 1. This will cover the individual who was tampering with the cassette with the mixture of ink and DNA.

Thus, as soon as the cassette 1 is tampered with, each of the bank notes 12 is covered not only in the indelible ink but also with the DNA.

In some variants of this embodiment, the ink reservoir 8 is collapsible and the pipe 6 leading from the canister 5 to the ink reservoir 8 is not provided. In these variants, the actuator 7 is situated on the canister and, when activated, releases the contents of the canister into the marking compartment 3. This collapses the ink reservoir 8 and forces the ink and DNA mixture out through the outlet pipe 9

It is to be understood that the cassette 1 is usually one of a plurality of such cassettes which together form a bank note storage system. When bank notes need to be transported, one of the cassettes is selected, loaded with bank notes and then transported to an ATM in which it is inserted. When a cassette has been legitimately emptied of bank notes it is returned.

The DNA that is stored in the ink reservoir 8 will now be described in greater detail. The DNA in the ink reservoir 8 comprises a plurality of single-stranded oligonucleotides, each of which is identical. In a bank note storage system, in which a number of separate cassettes 1 are provided, the oligonucleotides are provided with particular sequences. The oligonucleotides within each cassette 1 have the same sequence. However, comparing the oligonucleotide sequences of one cassette with those of other cassettes in the bank note storage system, each cassette has oligonucleotides with a variable central region such that each cassette contains DNA having a distinct and identifiable oligonucleotide sequence. However, the variable region of each oligonucleotide is flanked by first and second generic regions. The first generic region on every oligonucleotide in all the cassettes of the bank note storage system is the same and, similarly, the second generic region of the oligonucleotides in all of the cassettes of the bank note storage system is the same. A database of the sequences of all of the variable regions of the DNA markers and their respective cassette is maintained. When manufacturing the cassettes of a bank note storage system, a pool of sets of DNA oligonucleotides is provided, each set having a different variable region. A set of DNA oligonucleotides is selected from the pool and inserted into the ink reservoir 8 of one of the cassettes As an example, the oligonucleotides in one of the cassettes of the bank note storage system has the sequence of SEQ ID NO:1 and the oligonucleotides in another of the cassettes has the sequence of SEQ ID NO:2. As can be seen, the sequences have central variable regions (underlined), which are different from one another, flanked by generic regions at their 5' and 3' ends which are the same in both sequences. The generic regions and the variable region are designed such that there is minimal homology between the generic regions and the variable region. Minimal homology between two sequences is defined, in some embodiments of the invention, as when two or, in other embodiments, more than two consecutive nucleotides in one sequence are not present consecutively in the other sequence.

Therefore, in order to overcome this problem, in preferred embodiments of the present invention, an intercalating dye such as SyBr Green™ is added to the DNA sample during the

```
5' ACGTAGTAAAGAGGTGCCCGCCACTCGCTGTCGCAGATCATCGAGGGAAGACCACACGTGAGCCCAGAAC 3'    SEQ ID NO:1

5' ACGTAGTAAAGAGGTGCCCGCCATGACATCGTCTGAGATCGAGCTGGAAGACCACACGTGAGCCCAGAAC 3'    SEQ ID NO:2
```

Further explanation of these oligonucleotides is provided in WO-A-00/61799, which is incorporated herein by reference, in which they are referred to as Type III tags.

After the bank notes 12 have been marked with the indelible ink and the DNA, and have been recovered, the bank notes 12 are analysed in order to determine in which of the cassettes 1 they were originally stored. In order to analyse the marked bank notes, the DNA is extracted from the notes using a solvent, which is then removed and any components in the DNA which would inhibit PCR are also cleaned from the DNA. The DNA is then amplified using PCR. The primers used in order to amplify the DNA are complementary to the first and second generic regions of the oligonucleotides. Because there is no homology between generic regions and the variable region, there can be no "false priming" during PCR amplification by primers erroneously binding to parts of the variable region.

It is to be appreciated that, since the first and second generic regions are the same for the oligonucleotides in all of the cassettes in the bank note storage system, the same primers are used in order to amplify the oligonucleotide sequences no matter which cassette the bank notes come from in the storage system. Therefore, it is not necessary to know in advance from which cassette the bank notes come in order to carry out PCR amplification of the oligonucleotide sequences.

Once the DNA oligonucleotides have been amplified to a sufficient quantity, they are sequenced using methods well known in the art.

However, it has been discovered that in the synthesis of DNA oligonucleotides using conventional methods, a particular sample of marker oligonucleotides having a certain sequence is often contaminated with a very small amount of contaminating oligonucleotides having different sequences. These other oligonucleotides are the remains of previous synthesis reactions. In practice, when oligonucleotides are prepared for insertion into the cassettes of a bank note storage system, it is often the case that the contaminating oligonucleotides in a particular sample are the remains of oligonucleotides that were synthesised for other cassettes.

Thus, when the ink and DNA mixture is dispersed onto bank notes, the bank notes are covered with a certain amount of the contaminating oligonucleotides. Although the contaminating oligonucleotides are only present in very small quantities, it is to be noted that they have the same generic regions as the marker oligonucleotides and so they are also amplified in the PCR process. Because the initial quantity of contaminating oligonucleotides is much lower than that of the marker oligonucleotides, there is a time lag between significant amplification of the marker oligonucleotides and significant amplification of the contaminating oligonucleotides during PCR. Nevertheless, if the PCR process is allowed to run for too long, the quantity of contaminating oligonucleotides becomes sufficiently high that the contaminating sequences are also sequenced during the sequencing procedure. This leads to confusing results where two or more sequences are determined for a particular sample, either of which could be correct.

PCR process. The intercalating dye becomes visible under specific wavelengths of light in the presence of double-stranded DNA. The quantity of double-stranded DNA in the reaction is calculated during the PCR process by measuring the level of fluorescence of the intercalating dye under the illumination of light at the excitation wavelength of the dye. This gives an indication of the quantity of amplified DNA in the sample while the PCR process takes place. As soon as the quantity of amplified DNA has reached a level at which it can be sequenced, the PCR process is stopped so that the quantity of contaminating sequences in the sample does not reach a level that will affect the sequencing process. Thus only the nucleotide sequence of the marker oligonucleotides is determined.

By comparing the nucleotide sequence of the variable region that is determined against the database of the nucleotide sequences of the DNA in the cassettes in the bank note storage system, it is possible to determine which of the cassettes the bank notes have come from. It is therefore known that the bank notes have come from the theft of that particular cassette and the owner of the bank notes can be determined. With this information, it is possible to arrange reimbursement of the marked bank notes.

Furthermore, because DNA is sprayed upon the individual who tampered with the cassette, the clothes, or even the skin, of the individual can be analysed in a similar manner to the bank notes in order to establish that the individual tampered with the cassette. This can subsequently be used as evidence in court.

It is to be appreciated that to set up a bank note storage system, a different nucleotide sequence is required in the variable region of the DNA for each cassette. Therefore, if the storage system comprises ten thousand separate cassettes (in, for example, a delocalised storage system), it is necessary for the variable region of the oligonucleotides to be long enough such that it is able to encode at least ten thousand separate sequences. Even so, the variable region of the oligonucleotides need not be particularly long. A variable region of twelve nucleotides would be more than adequate for most purposes. However, if relatively short variable regions are used, particular sequencing methods are utilised in order to determine the sequence since traditional sequencing methods may not be capable of accurately sequencing such a short oligonucleotide.

For example, in some embodiments of the invention, Pyrosequencing™ is used. This technique is described in greater detail in WO-A-98/13523, WO-A-98/28440, WO-A-00/43540, EP-A-1141401 and WO-A-02/85341 which are incorporated herein by reference. In these embodiments, the variable region of each of the oligonucleotides is synthesised such that each nucleotide is always adjacent to a different type of nucleotide. Thus, for example, if the first nucleotide in the variable region is A then this may be followed by C, G or T, but not another A. This ensures that there are no consecutively repeated nucleotides thereby simplifying the sequence interpretation. The variability possible in the variable region is somewhat reduced by this approach (only $3^n$ sequences are possible instead of $4^n$, where n is the length of the sequence)

but oligonucleotides having sufficient length to encode the requisite number of sequences can easily be synthesised.

As explained above, the generic regions and the variable region are designed such that there is minimal homology between the generic regions and the variable region. This is achieved in these embodiments by including nucleotide repeats in the generic regions, which, as has been explained above, do not exist in the variable region.

In alternative embodiments of the invention, the DNA oligonucleotides do not comprise a central variable region flanked by two generic regions as described above. In some of these alternative embodiments, the DNA oligonucleotides comprise a variable region adjacent a generic region (referred to as a Type I tag in the nomenclature of WO-A-00/61799). In other embodiments, the DNA oligonucleotides comprise two adjacent variable regions (referred to as a Type II tag in WO-A-00/61799). In these embodiments, the above described method of DNA amplification is adapted, as will now be described, to provide a plurality of different primers.

In DNA amplification relating to bank note storage systems wherein Type I tags are used, a plurality of different primers, each complementary to one of the various variable regions and primers complementary to the generic region are provided. PCR amplification of the DNA oligonucleotide is then carried out with all of the primers present, to ensure that amplification takes place no matter which variable region sequence the oligonucleotide has. The amplified oligonucleotides are then sequenced.

However, in a variation of this embodiment, the DNA oligonucleotides are first divided into a plurality of different samples. To each sample is added primers complementary to one of the possible variable regions and primers complementary to the generic region. The PCR process is then carried out although this is only successful in the sample in which the primers complementary to the variable region of the particular DNA oligonucleotide are present. In other samples, no complementary primer is present to prime the DNA polymerase and so DNA amplification does not take place. By determining in which sample PCR amplification has been successful and noting the particular variable region primer that was used in that sample, it is possible to determine the sequence of the DNA oligonucleotide without a separate sequencing step.

In bank storage systems wherein Type II tags are used, PCR amplification of the DNA oligonucleotides is carried out by adding a plurality of primers, each complementary to one of the various variable regions. PCR amplification of the DNA oligonucleotides is then carried out although only the primers which are actually complementary to the variable regions of the DNA oligonucleotide function in the PCR process. Once DNA amplification has been completed, the DNA oligonucleotide is sequenced as described previously.

In a variation of this embodiment, the DNA oligonucleotides are initially divided into a plurality of samples. Before the amplification process, a different pair of primers is added to each sample, each primer being complementary to one of the possible variable regions of the DNA oligonucleotide. Amplification of the DNA oligonucleotides only takes place in that sample which is provided with primers which are complementary to the variable regions of the DNA oligonucleotide. Thus, by noting the sequence of the primers that were added to the sample which was amplified, it is possible to identify the particular DNA oligonucleotide without sequencing the oligonucleotide as such.

In some further embodiments of the present invention (in which Type I, Type II or Type III DNA oligonucleotides may be used) the DNA oligonucleotide is not identified by sequencing the oligonucleotide as such. In these embodiments, a DNA oligonucleotide micro array is used to identify the DNA oligonucleotide. Such DNA micro arrays are known in the art and are, for example, disclosed in EP-A-0373203, which is incorporated herein by reference.

The micro array comprises a substrate to which is attached a plurality of single stranded test oligonucleotides of different sequences, in an array. When it is necessary to identify a DNA oligonucleotide, from a DNA sample removed from a bank note, a label (such as a fluorescent label or a radioactive isotope) is attached to each DNA oligonucleotide in the sample. The sample of labelled DNA oligonucleotides is then applied to the substrate under conditions which are sufficiently stringent such that there is hybridization between the labelled DNA oligonucleotides and the test oligonucleotides attached to the substrate only if the oligonucleotides are complementary to each other along the entire length of the test oligonucleotide. Non-hybridized oligonucleotides are subsequently washed away. The position of the hybridized oligonucleotides is then determined by the location of the label on the array. By selecting the length and sequence of the test oligonucleotides carefully, it is possible for the pattern of hybridizing oligonucleotides to identify exactly a particular sequence. By relating together the sequences of the test oligonucleotides that hybridized to the sample DNA oligonucleotide, it is possible to determine the sequence of the sample DNA oligonucleotide.

However, even this step is unnecessary in certain embodiments in which each sequence of oligonucleotide in a bank note storage system is accorded a security code which uniquely identifies the oligonucleotide. The security code is associated with a related database entry including information such as the particular ATM cassette in which the oligonucleotide is stored. The pattern of the hybridized oligonucleotides in the array is, as has previously been described, indicative of a particular oligonucleotide. A record is kept of each pattern of hybridization and the security code of the corresponding oligonucleotide which forms that pattern of hybridization. When an oligonucleotide is analyzed on the micro array, a pattern of hybridization is formed which is then compared with the record to determine the security code and identify oligonucleotide. Thus, it is possible to identify a particular DNA oligonucleotide marker without sequencing the oligonucleotide as such.

Figure 2:
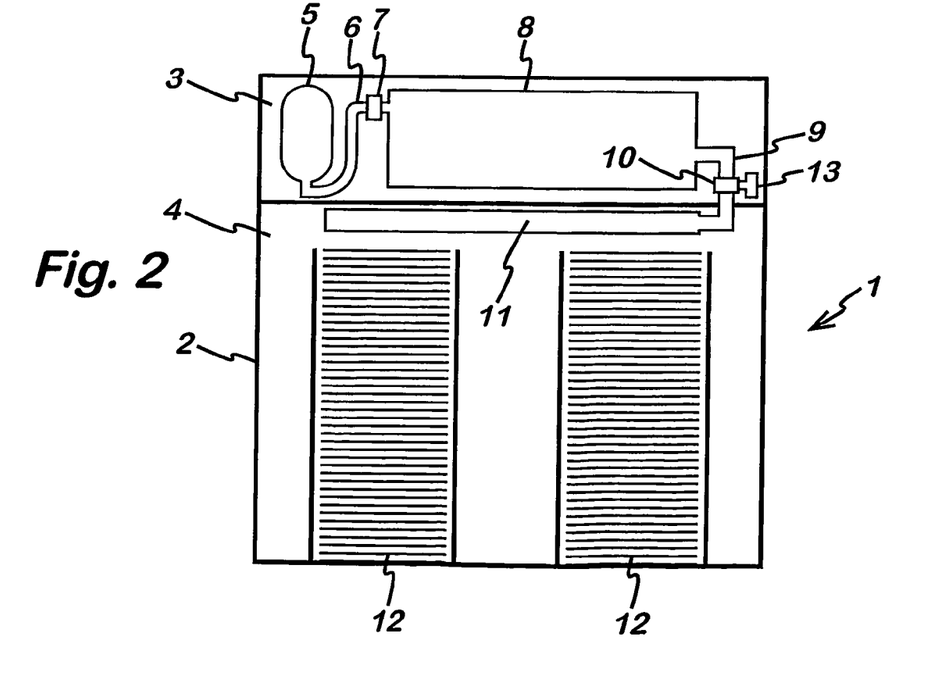
FIG. 2 is a cross-sectional view of a bank note cassette in accordance with another embodiment of the present invention.

In the above described embodiments of the invention, the DNA is stored with the ink in the reservoir 8 under normal circumstances. However, in some alternative embodiments of the invention, this is not the case. Referring to FIG. 2, a cassette 1 in accordance with such an alternative embodiment is shown, in which like components are given the same numbers. This embodiment of the invention is the same as the previous embodiments except that the reservoir 8 contains only the indelible ink and no DNA. Instead, a separate DNA reservoir 13 is provided, connected to the pressure valve 10. The DNA reservoir 13 contains 1 ml of a mixture of DNA in a buffer.

In use, this embodiment functions in the same way as the previous embodiment, and the contents of the marking compartment 3 do not operate under normal circumstances. If the cassette 1 is tampered with then, as with the previous embodiment, the compressed gas is released from the canister 5 thus increasing the pressure in the reservoir 8. When the pressure in the reservoir 8 reaches a predetermined level, the pressure valve 10 is released, allowing the simultaneous passage of ink through the outlet pipe 9 into the dispersing arm 11 together with the mixing therein of the DNA contained in the second reservoir 13. Thus, in this embodiment, a mixture of the ink 8 and the DNA is formed only when the marking mechanism is activated. This can be advantageous in embodiments in which the ink degrades the DNA and also has the advantage that the particular DNA stored in a cassette 1 can be changed without requiring the reservoir of ink 8 also to be changed.

In some types of bank note cassettes, a marking mechanism other than an ink marking mechanism is used. In particular, in some embodiments a "smoke and dye" marking mechanism is used instead. In these embodiments, the contents of the marking compartment 3 and the dispersing arm 11 are not provided as has been described in the previous embodiments. Instead, one or more pyrotechnic devices are provided in the cassette 1. Such pyrotechnic devices are known to those skilled in the art.

Figure 3:
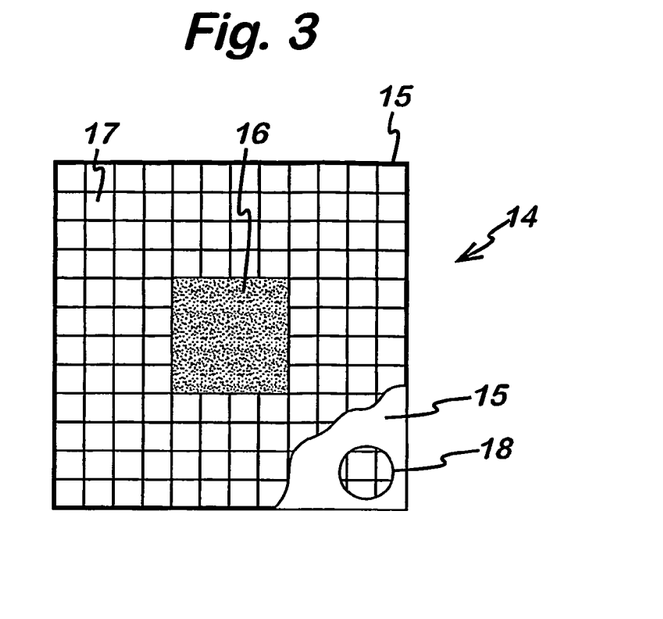
FIG. 3 is a plan view, with part cut away, of a portion of a bank note cassette in accordance with a further embodiment of the invention.

Referring to FIG. 3 a pyrotechnic device 14 comprises an outer housing 15 in the centre of which is located a section of sand 16. An array of smoke pellets 17 is packed around the section of sand 16 within the housing 15. The smoke pellets 17 have an indelible dye incorporated into them.

FIG. 3 depicts part of the top of the housing 15 cut away so that the interior of the pyrotechnic device 14 can be seen. However, as is shown at the bottom righthand corner of the device, the housing 15 covers all of the exterior of the device except for an aperture 18 that is provided in the housing of the pyrotechnic device 14. During manufacture, DNA oligonucleotides are added to the pyrotechnic device by dripping between 200 μl and 1 ml of a solution of DNA in a mixture of 75% alcohol and 25% water through the aperture 18. On contact with the array of smoke particles 17 beneath the aperture 18 the solutions diffuse across the array until the DNA has soaked into each of the smoke pellets 17.

In use of this embodiment, the pyrotechnic device 14 is inactive under normal circumstances, it being possible for bank notes 12 to be removed from the cassette 1 when they are dispensed properly while it is in an ATM. However, if the housing of the cassette 1 is tampered with, a detector (not shown) sends a signal to the pyrotechnic device 14 which activates the pyrotechnic device. Upon activation, the smoke pellets 17 undergo an exothermic reaction. The smoke pellets 17 very rapidly generate a large quantity of smoke, in which the dye and the DNA oligonucleotides are mixed. The smoke builds up inside the housing 15 but can only escape through the aperture 18. Thus the pyrotechnic device 14 not only acts as a means to release the smoke but also as a distribution mechanism for the smoke, dye and DNA mixture. Because the smoke is a fluid and behaves accordingly and because it is generated in such large quantities, it very quickly permeates throughout the interior of the cassette 1 and comes into contact with each of the bank notes 12. The smoke carries the dye as well as the DNA and so each of the bank notes is marked with both the dye and the DNA.

Furthermore, some of the smoke is released from the cassette 1 and this covers the individual who tampered with the cassette with a mixture of the dye and DNA.

Following the marking of the bank notes in this way, the bank notes can be analysed as is described in the previous embodiments. Similarly, the clothes, or even the skin, of the individual can be analysed as previously described.

In an alternative version of the "smoke and dye" embodiments of the invention, the DNA oligonucleotides are not added to the pyrotechnic device 14 directly. Instead, the DNA oligonucleotides are first added to or incorporated within a plurality of micron or sub-micron sized carrier particles. In some embodiments, these carrier particles are made from polymers. In other embodiments, the carrier particles are inorganic in composition, being made, for example, from talc (magnesium silicate hydroxide).

Figure 4:
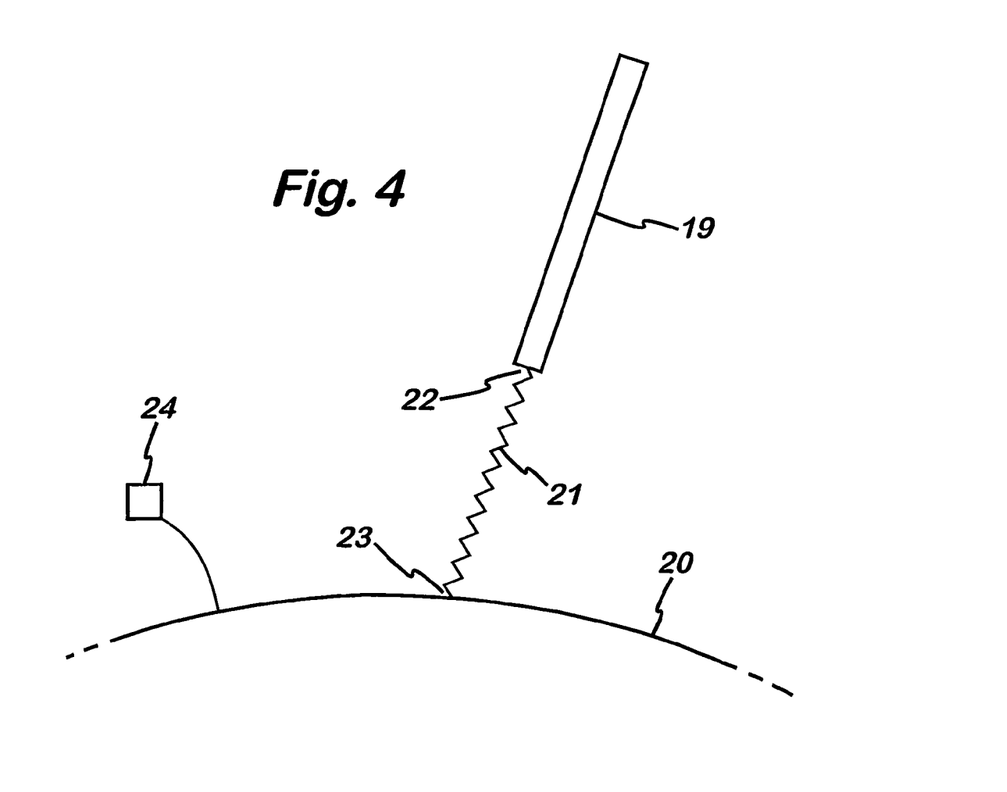
FIG. 4 is a schematic view of a DNA oligonucleotide attached to a particle via a linker in accordance with a portion of a further embodiment of the invention.

Referring to FIG. 4, a preferred embodiment of such a version is shown schematically, although only a portion of the surface of the particle is depicted. Each DNA oligonucleotide 19 is bonded to a carrier particle 20 by a linker molecule 21 such as a $C_{12}$-$C_{16}$ alkyl group. The linker molecule 21 is bound, at one end 22, to the DNA oligonucleotide 19 and, at the other end 23, has a covalent bond with the particle 20. However, in some other embodiments, the DNA oligonucleotides are bound directly to the particles through ionic interactions or by passive adsorption.

In particularly preferred embodiments which use carrier particles, a fluorescent label 24 is also attached to each carrier particle 20.

The advantage of attaching the DNA oligonucleotides 19 to carrier particles 20 is that it assists in the general identification of bank notes 12 which are marked with DNA oligonucleotides 19, especially when the carrier particles 20 are also marked with a fluorescent label 24.

In use, the bank notes 12 are first visualised (e.g. by subjecting them to ultraviolet light) in order to determine whether or not the fluorescent label 24 can be seen. If the fluorescent label is present then not only is the bank note 12 identified as being one which is labelled with the DNA oligonucleotide 19 but the particular area of the bank note 12 which has been so marked is also pinpointed. The steps of DNA amplification and sequencing can then be carried out as previously described. Thus the use of a fluorescent label 24 on the carrier particle 20 avoids the need for DNA amplification and sequencing of every bank note that is recovered, which would be unnecessary if the bank notes are ultimately found not to have been marked with a DNA oligonucleotide.

In the embodiments in which the DNA oligonucleotide 19 is attached to the particle 20 via a linker molecule 21 of sufficient length (such as the $C_{12}$-$C_{16}$ alkyl group described above) then steric hindrance of the DNA oligonucleotide 19 adjacent the particle 20 is avoided and the steps of amplification and sequencing of the DNA oligonucleotide 19 can be carried out without removing each oligonucleotide 19 from its respective carrier particle 20.

In the embodiments in which the DNA oligonucleotide 19 is attached directly to the particle 20 through an ionic interaction or by passive adsorption then each DNA oligonucleotide 19 is first released from its respective particle 20 by putting the particles 20 and DNA oligonucleotides 19 in a buffer and changing the ionic strength of the buffer, such as by changing its pH. Once each DNA oligonucleotide 19 has been released from its particle 20, the amplification and sequencing steps are carried out as previously described.

In the above described embodiments of the invention, amplification of the DNA oligonucleotides is carried out using the PCR process. However, in other embodiments of the invention, different amplification processes are used. For example, in some embodiments, a thermal cycling nucleic acid amplification technique other than PCR is used. In some other embodiments of the invention, an isothermal amplification technique is used to amplify the number of copies of the DNA oligonucleotide.

It is to be appreciated that, while the above embodiments have been described in relation to cassettes carrying bank notes, in alternative embodiments the cassette 1 carries other, similar, valuable items instead such as bank bonds or store vouchers.

It is to be understood that in certain variants of the above embodiments, the marking compartment 3 is a separate module that is detachable from the bank note storage compartment 4. In these variants, a locking mechanism is provided between the marking compartment module and the bank note storage compartment 4 to lock the two compartments together. Attempts to tamper with the locking mechanism will trigger the release of the ink or smoke and dye and DNA mixture.

The above described embodiments of the invention relate to a cassette for insertion into an ATM. However, in other embodiments of the invention a different type of cassette is provided or even a different type of marking apparatus. For example, in one embodiment, the cassette is of a type for the transfer of bank notes between banks and no provision is made for insertion into an ATM. In another embodiment, the marking apparatus is a brief case which comprises a marking compartment 3 and bank note storage compartment 4 substantially as described above except that the bank note storage compartment 4 is not adapted for insertion into an ATM and is, instead, accessible from within the brief case.

In a particularly preferred variant of the "smoke and dye" embodiment, instead of an ATM cassette, a money dye pack is provided. This pack is stored in the drawer of a human bank teller in a bank, and, in the event of a robbery, is handed over to the thief. Instead of being activated by a tamper sensor, the release of the ink or smoke and dye and DNA mixture is triggered by the pack leaving the confines of the bank.

In other respects, these embodiments work in a similar manner as the previously described embodiments.

generic region and a second generic region, the first and second generic regions being the same in each nucleic acid marker of each marking apparatus and the variable region being different in the nucleic acid marker of each marking apparatus, the variable region of each nucleic acid marker containing no consecutively repeated nucleotides.

2. A storage system according to claim 1, wherein each item is one or more bank notes, each means to release the marking fluid being activatable to release the visibly staining marking fluid such that the mixture of the nucleic acid marker and the visibly staining marking fluid is dispersed onto the one or more bank notes.

3. A storage system according to claim 2, wherein each marking apparatus is an automated teller machine cassette.

4. A storage system according to claim 1, wherein each means to release the visibly staining marking fluid comprises a marking fluid reservoir of visibly staining marking fluid.

5. A storage system according to claim 4, wherein the visibly staining marking fluid comprises an indelible ink.

6. A storage system according to claim 5, wherein the nucleic acid marker is mixed in with the indelible ink.

7. A storage system according to claim 6, wherein each marking apparatus further comprises a nucleic acid reservoir containing the nucleic acid marker, the nucleic acid reservoir being coupled to the distribution mechanism such that when

The invention claimed is:

1. A storage system comprising a plurality of marking apparatuses for marking an item, wherein each marking apparatus comprises: means to receive the item; a nucleic acid marker; means to release a visibly staining marking fluid; and a distribution mechanism coupled to the nucleic acid marker and the means to release the visibly staining marking fluid, the means to release the visibly staining marking fluid being activatable to release the visibly staining marking fluid such that the distribution mechanism disperses a mixture of the nucleic acid marker and the visibly staining marking fluid onto the item, wherein each nucleic acid marker has a variable region of at least twelve nucleotides in length flanked by a first the marking fluid reservoir is activated, the distribution mechanism mixes the visibly staining marking fluid and the nucleic acid marker.

8. A storage system according to claim 1, wherein each means to release the visibly staining marking fluid comprises one or more smoke pellets, the visibly staining marking fluid comprising smoke.

9. A storage system according to claim 8, wherein the means to release the visibly staining marking fluid and the distribution mechanism of each marking apparatus comprises a pyrotechnic device containing the one or more smoke pellets.

10. A storage system according to claim 1, wherein the nucleic acid marker comprises a plurality of single-stranded DNA oligonucleotides.

11. A storage system according to claim 1, wherein each marking apparatus further comprises a detector connected to the means to release the visibly staining marking fluid, the detector activating the means to release the visibly staining marking fluid in response to detecting tampering with the marking apparatus.

12. A storage system according to claim 1, wherein each marking apparatus further comprises a plurality of carrier particles to which the nucleic acid marker is attached.

13. A storage system according to claim 12, wherein the carrier particles are made from a polymer.

14. A storage system according to claim 12, wherein the carrier particles are made from an inorganic compound.

15. A storage system according to claim 12, wherein the nucleic acid marker is attached to the carrier particles via a covalent bond.

16. A storage system according to claim 15, wherein each nucleic acid marker molecule is bonded to a linker molecule, the linker molecule having a covalent bond to a carrier particle.

17. A storage system marking apparatus according to claim 16, wherein the linker molecule is a $C_{12}$-$C_{16}$ alkyl group.

18. A storage system according to claim 12, wherein the nucleic acid marker is attached to the carrier particles via ionic interactions or passive adsorption.

19. A storage system according to claim 12, further comprising a fluorescent label attached to each of the carrier particles.

20. A method of security marking an item with a marking apparatus in response to detecting tampering with the marking apparatus comprising the steps of: providing a mixture of a nucleic acid marker and a visibly staining marker fluid; and dispersing the mixture onto the item, wherein each nucleic acid marker of the mixture has a variable region of at least twelve nucleotides in length flanked by a first generic region and a second generic region, the first and second generic regions being the same in each nucleic acid marker and the variable region being different in the nucleic acid marker of the marking apparatus compared to that of another marking apparatus, wherein the variable region of each nucleic acid marker contains no consecutively repeated nucleotides, and wherein the item is a bank note or similar valuable item.

21. A method according to claim 20, further comprising the step of identifying the nucleic acid marker.

22. A method according to claim 20, further comprising, prior to providing the mixture of the nucleic acid marker and the visibly staining marker fluid, selecting the nucleic acid marker from a pool of nucleic acid markers, each nucleic acid marker in the pool having a respective variable region flanked by a first generic region and a second generic region, the first and second generic regions being the same in each of the nucleic acid markers in the pool and the variable region being different in each nucleic acid marker in the pool.

23. A method of analyzing an item that has been rendered unusable by being marked with a marking apparatus by a visibly staining marker fluid and a nucleic acid marker, comprising the step of identifying the nucleic acid marker; wherein the nucleic acid marker has a variable region of at least twelve nucleotides in length flanked by a first generic region and a second generic region, the first and second generic regions being the same in each nucleic acid marker and the variable region being different in the nucleic acid marker of the marking apparatus compared to that of another marking apparatus, wherein the variable region of each nucleic acid marker contains no consecutively repeated nucleotides, and wherein the item is a bank note or similar valuable item.

24. A method according to claim 21 or 23 wherein the step of identifying the nucleic acid marker comprises sequencing at least a portion of the nucleic acid marker.

25. A method according to claim 21 or 23 wherein the step of identifying the nucleic acid marker comprises: providing a plurality of test oligonucleotides; applying the nucleic acid marker to the test oligonucleotides under conditions such that the nucleic acid marker hybridizes to test oligonucleotides to which it is complementary; and determining the test oligonucleotide or oligonucleotides to which the nucleic acid marker has hybridized.

26. A method according to claim 25 wherein the test oligonucleotides are attached to a substrate in an array formation.

27. A method according to claim 20 or 23 further comprising the step of amplifying the number of copies of the nucleic acid marker prior to the step of identifying the nucleic acid marker.

28. A method according to claim 27, wherein the amplifying step comprises using thermal cycling nucleic acid amplification to amplify the number of copies of the nucleic acid marker.

29. A method according to claim 28, wherein the thermal cycling nucleic acid amplification is polymerase chain reaction (PCR).

30. A method according to claim 27, wherein the amplifying step comprises using an isothermal amplification technique.

31. A method according to claim 29, further comprising the step of measuring the quantity of amplified nucleic acid in the PCR during the amplifying step and stopping the amplification after the quantity of amplified nucleic acid reaches a predetermined threshold.

32. A method according to claim 31, wherein the step of measuring the quantity of amplified nucleic acid comprises the step of adding an intercalating dye to the amplified nucleic acid.

33. A method according to claim 20 or 23, wherein the nucleic acid marker comprises a plurality of single-stranded DNA oligonucleotides.

34. A method according to claim 33, wherein the single-stranded DNA oligonucleotide comprises a variable region flanked by a first generic region and a second generic region, wherein there is minimal homology between the variable region and the first and second generic regions.

35. A method according to claim 34, wherein the variable region contains no consecutively repeated nucleotides.

36. A marking apparatus for marking an item, the marking apparatus comprising: (a) a pyrotechnic device containing one or more smoke pellets; (b) a dye; and (c) a nucleic acid marker having a variable region of at least twelve nucleotides in length flanked by a first generic region and a second generic region, the first and second generic regions being the same in each nucleic acid marker and the variable region being different in the nucleic acid marker of the marking apparatus compared to that of another marking apparatus, wherein the dye and the nucleic acid marker are impregnated into the one or more smoke pellets, the pyrotechnic device is activatable to release a mixture of smoke, the dye, and the nucleic acid marker, and the variable region of each nucleic acid marker contains no consecutively repeated nucleotides.

37. A method of producing a marking apparatus comprising:
  (a) providing a pyrotechnic device containing one or more smoke pellets having a dye incorporated therein;
  (b) preparing a mixture of a nucleic acid marker and a solvent, wherein each nucleic acid marker has a variable region of at least twelve nucleotides in length flanked by a first generic region and a second generic region, the first and second generic regions being the same in each nucleic acid marker and the variable region being different in the nucleic acid marker of the marking apparatus compared to that of another marking apparatus, and wherein the variable region of each nucleic acid marker (i) contains no consecutively repeated nucleotides or (ii) contains sequences of three consecutive nucleotides that are not present as sequences of consecutive nucleotides in either generic region; and
  (c) positioning the mixture on to at least one of the one or more smoke pellets such that the mixture diffuses through the one or more smoke pellets.

38. A method according to claim 37 wherein the mixture comprises between 60 and 90% alcohol and between 10 and 40% water.

39. A method according to claim 20 or 23, wherein the item is a bank note, a credit note, a cellular phone recharging card, a ticket, a document, a bank bond, or a store voucher.

40. A storage system according to claim 14, wherein the inorganic compound is magnesium silicate hydroxide.

41. A storage system comprising a plurality of marking apparatuses for marking an item, wherein each marking apparatus comprises: means to receive the item; a nucleic acid marker; means to release a visibly staining marking fluid; and a distribution mechanism coupled to the nucleic acid marker and the means to release the visibly staining marking fluid, the means to release the visibly staining marking fluid being activatable to release the visibly staining marking fluid such that the distribution mechanism disperses a mixture of the nucleic acid marker and the visibly staining marker fluid onto the item, wherein each the nucleic acid marker has a variable region of at least twelve nucleotides in length flanked by a first generic region and a second generic region, the first and second generic regions being the same in each nucleic acid marker of each marking apparatus and the variable region being different in the nucleic acid marker of each marking apparatus, and wherein sequences of three consecutive nucleotides in each variable region are not present as sequences of consecutive nucleotides in either generic region.

* * * * *

UNITED STATES PATENT AND TRADEMARK OFFICE
CERTIFICATE OF CORRECTION

| | | |
|---|---|---|
| PATENT NO. | : 8,783,194 B2 | Page 1 of 1 |
| APPLICATION NO. | : 10/508416 | |
| DATED | : July 22, 2014 | |
| INVENTOR(S) | : Robert Sleat and Greg Van Lint | |

It is certified that error appears in the above-identified patent and that said Letters Patent is hereby corrected as shown below:

In the Claims

Column 14, Claim 7, Line 22, replace "claim 6" with --claim 4--.

Column 18, Claim 41, Line 16, replace "each the nucleic acid" with --each nucleic acid--.

Signed and Sealed this
Thirtieth Day of December, 2014

Michelle K. Lee
*Deputy Director of the United States Patent and Trademark Office*

SEQUENCE LISTING

```
<160> NUMBER OF SEQ ID NOS: 2

<210> SEQ ID NO 1
<211> LENGTH: 70
<212> TYPE: DNA
<213> ORGANISM: Artificial Sequence
<220> FEATURE:
<223> OTHER INFORMATION: Synthetic

<400> SEQUENCE: 1
acgtagtaaa gaggtgcccg ccactcgctg tcgcagatca tcgagggaag accacacgtg      60
agcccagaac                                                            70

<210> SEQ ID NO 2
<211> LENGTH: 70
<212> TYPE: DNA
<213> ORGANISM: Artificial Sequence
<220> FEATURE:
<223> OTHER INFORMATION: Primer

<400> SEQUENCE: 2
acgtagtaaa gaggtgcccg ccatgacatc gtctgagatc gagctggaag accacacgtg      60
agcccagaac                                                            70
```